United States Patent
Quinn et al.

Patent Number: 6,036,654
Date of Patent: Mar. 14, 2000

[54] MULTI-LUMEN, MULTI-PARAMETER CATHETER

[75] Inventors: Michael D. Quinn, Plano, Tex.; Jaime Simán, Santa Ana, Calif.; Mark L. Yelderman, Plano, Tex.

[73] Assignee: Baxter International Inc., Deerfield, Ill.

[21] Appl. No.: 08/311,477

[22] Filed: Sep. 23, 1994

[51] Int. Cl.⁷ ........................................................ A61B 5/02
[52] U.S. Cl. .......................... 600/526; 600/504; 600/549; 600/339; 607/17; 604/93; 604/282
[58] Field of Search .................................. 128/632, 634, 128/664–7, 672, 673, 691, 692, 713, 736, 693; 607/17, 21, 23; 600/339, 309, 310, 473–479, 485, 486, 504, 526, 549; 604/264, 280, 282, 93

[56] References Cited

U.S. PATENT DOCUMENTS

| | | |
|---|---|---|
| 4,178,936 | 12/1979 | Newcomb . |
| 4,406,656 | 9/1983 | Hattler et al. . |
| 4,574,173 | 3/1986 | Bennett . |
| 4,718,423 | 1/1988 | Willis et al. ............................ 128/713 |
| 4,729,409 | 3/1988 | Paul . |
| 4,753,640 | 6/1988 | Nichols et al. . |
| 4,776,340 | 10/1988 | Moran et al. ........................... 128/634 |
| 4,813,429 | 3/1989 | Eshel et al. . |
| 4,838,881 | 6/1989 | Bennett . |
| 4,901,734 | 2/1990 | Griffin et al. . |
| 4,941,475 | 7/1990 | Williams et al. . |
| 4,975,055 | 12/1990 | LaPlante . |
| 5,158,540 | 10/1992 | Wijay . |
| 5,167,623 | 12/1992 | Cianci et al. . |
| 5,176,144 | 1/1993 | Yoshikoshi et al. . |
| 5,209,741 | 5/1993 | Spaeth . |
| 5,378,230 | 1/1995 | Mahurkar . |
| 5,435,308 | 7/1995 | Gallup et al. ........................... 128/713 |

FOREIGN PATENT DOCUMENTS

| | | |
|---|---|---|
| 0 226 220 | 6/1987 | European Pat. Off. . |
| 0 417 781 | 3/1991 | European Pat. Off. . |
| 2 513 520 | 9/1981 | France . |

*Primary Examiner*—Linda C. M. Dvorak
*Assistant Examiner*—Bryan K. Yarnell
*Attorney, Agent, or Firm*—Bruce M. Canter; Guy L. Cumberbatch; Lena I. Vinitskaya

[57] ABSTRACT

A multi-lumen catheter capable of measuring cardiac output continuously, mixed venous oxygen saturation as well as other hemodynamic parameters. The catheter is also capable of undertaking therapeutic operations such as drug infusion and cardiac pacing. The catheter includes optical fibers for coupling to an external oximeter, an injectate port and thermistor for bolus thermodilution measurements, a heating element for inputting a heat signal and for coupling to an external processor for continuously measuring cardiac output, and a distal lumen for measuring pressure, withdrawing blood, guidewire passage or drug infusion. In a preferred embodiment, the catheter includes a novel lumen configuration permitting an additional infusion lumen for either fast drug infusion or cardiac pacing.

15 Claims, 4 Drawing Sheets

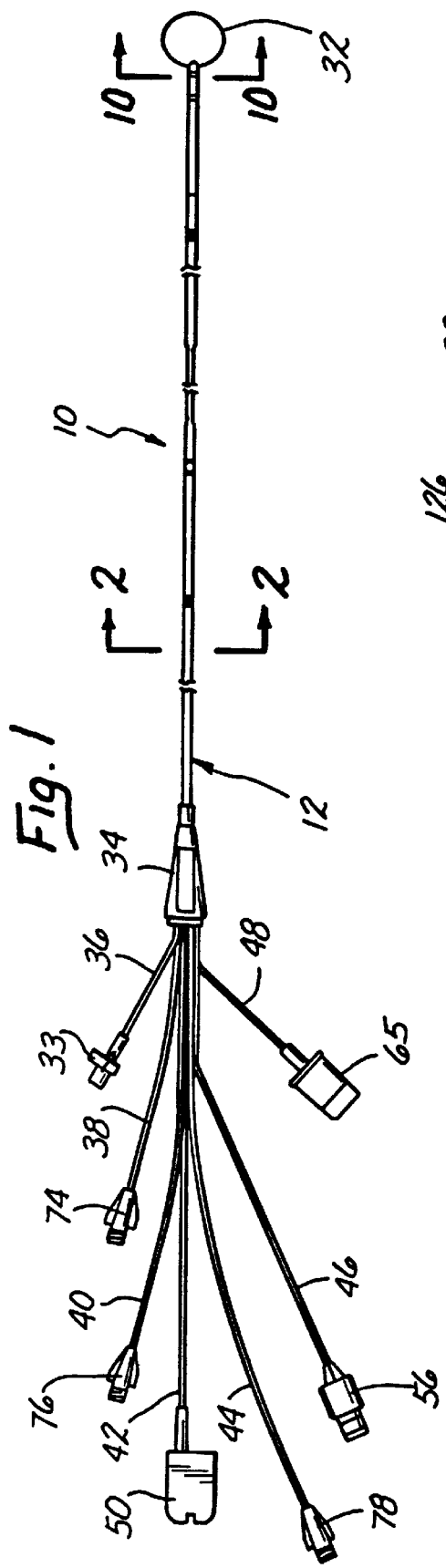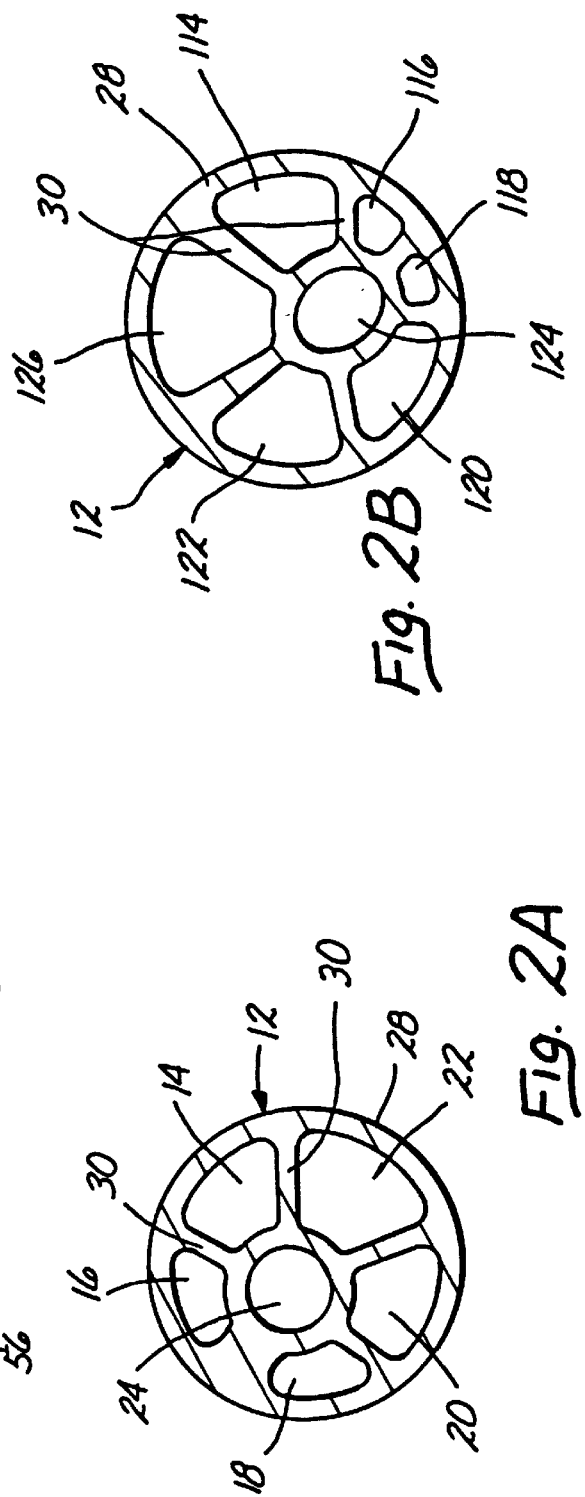

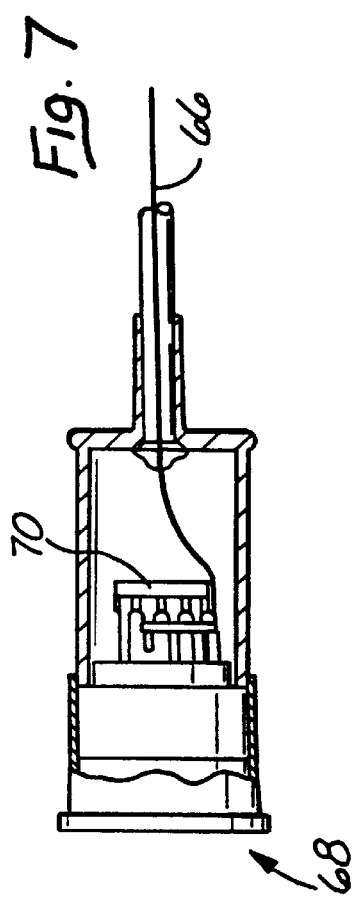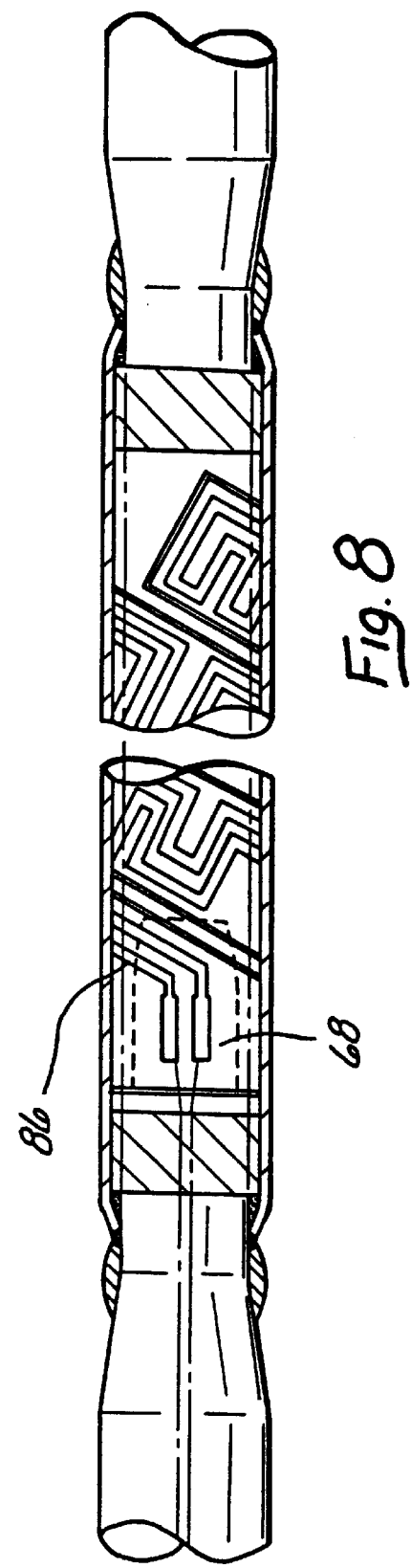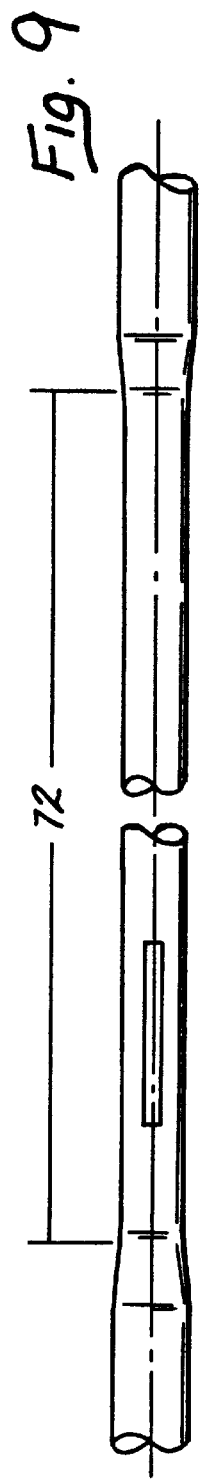

MULTI-LUMEN, MULTI-PARAMETER CATHETER

BACKGROUND OF THE INVENTION

1. Field of the Invention

The present invention relates to multi-lumen catheters, more particularly, to a multi-lumen catheter capable of measuring cardiac output continuously, mixed venous oxygen saturation as well as other hemodynamic parameters. The catheter is also capable of undertaking therapeutic operations such as drug infusion and cardiac pacing.

2. Description of the Prior Art

As is well known, catheters have been developed for purposes of measuring various specific hemodynamic parameters, such as blood pressure, cardiac output, right heart ejection fraction, and mixed venous oxygen saturation, as well as to infuse medication, withdraw blood or to pace the heart.

Cardiac catheters having flotation balloons and which measure cardiac output using the bolus thermodilution technique are well known in the art, as disclosed for example in U.S. Pat. No. 4,508,123, to Wyatt et al. Additionally, catheters having optical fibers connected to light emitting and receiving means and to signal processing/displaying means have been used to measure oxygen saturation in blood (i.e. SvO2), as disclosed in U.S. Pat. No. 4,651,741 to Passafaro. More recently, catheters have been designed with resistance heaters for the purpose of monitoring cardiac output on a continuous basis. An example of such a catheter is disclosed in U.S. patent application Ser. No. 08/049,231, to Quinn et al.

To date, however, no one has designed a catheter that is capable of measuring the aforementioned hemodynamic parameters without having to remove and reinsert multiple catheters and probes. Specifically, no one has designed a flotation balloon catheter having a resistance heater and a lumen for housing optical fibers to measure cardiac output continuously and to measure mixed venous oxygen saturation.

SUMMARY OF THE INVENTION

What is needed and what is provided by the present invention is a multi-lumen, multi-parameter catheter that is capable of monitoring cardiac output continuously as well as measuring mixed venous oxygen saturation in blood. In addition, the invention allows for determination of cardiac output using conventional bolus thermodilution techniques as well as providing drug infusion, cardiac pacing, pressure monitoring, blood withdrawal, and guidewire passage.

These features are accomplished by a unique catheter lumen configuration which can be easily extruded, molded or cast by conventional plastic processing operations. The catheter configuration provides for a novel fiber optic lumen for the SvO2 measurement, a balloon inflation lumen for catheter flotation, a thermistor wire lumen for measuring blood temperature, a bolus injectate lumen for bolus thermodilution, a heater wire lumen for the continuous cardiac output heater, and a distal lumen for drug infusion, pressure monitoring, blood withdrawal, and guidewire passage.

The present invention thus comprises a pulmonary artery balloon catheter including the aforementioned lumen configuration which can house all of the components required for the catheter to perform all of the aforementioned functions, including optical fibers, a thermistor and associated leads, and a heating filament and associated heater wiring. The catheter further comprises means to connect the catheter to a monitor or instrument for calculating and displaying the aforementioned hemodynamic parameters, such as a fiber optic connector which interfaces the fibers with the monitor, as well as various other interfacing means which are well known in the art.

In a preferred embodiment of the invention, the catheter further includes a venous infusion port lumen for fast infusion of solutions into the bloodstream. Alternatively, the venous infusion port lumen can be utilized for cardiac pacing.

The present invention thus provides a catheter which is capable of monitoring various hemodynamic parameters without having to remove and reinsert numerous catheters or probes with the concomitant risks and inconveniences associated with such multiple procedures. The catheter of the present invention is also capable of combining monitoring features with therapeutic features in that the catheter is capable of infusing drugs or pacing the heart in addition to hemodynamic monitoring.

BRIEF DESCRIPTION OF THE DRAWINGS

The above and other objects and advantages of the invention will become more apparent and more readily appreciated from the following detailed description of the presently preferred exemplary embodiments of the invention taken in conjunction with the accompanying drawings, of which:

FIG. 1 illustrates a side elevational view of the multi-lumen catheter of the present invention;

FIG. 2A illustrates a cross-sectional view of a first preferred embodiment of a six lumen catheter of the present invention taken along the lines 2—2 of FIG. 1;

FIG. 2B illustrates a cross-sectional view of a second preferred embodiment of a seven lumen catheter of the present invention taken at an analogous point along the catheter as FIG. 2A, showing a novel lumen configuration;

FIG. 7 illustrates a side elevational, partially sectioned view of the heater connector for use with the catheter of FIG. 1;

FIG. 8 illustrates an enlarged side elevational of a preferred heater element wrapped around the catheter of FIG. 1;

FIG. 9 illustrates a side elevational view of the stepped down region of the catheter of FIG. 1;

DETAILED DESCRIPTION OF THE INVENTION

Figure 3:
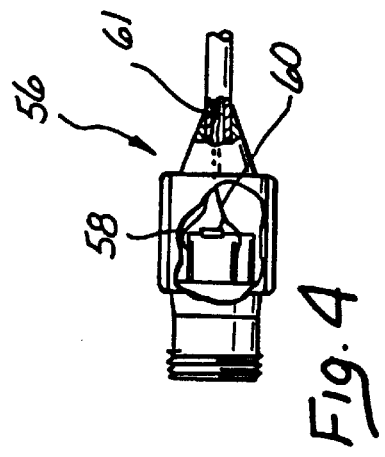
FIG. 3 illustrates a plan view of an optical connector for use with the catheter of FIG. 1.

A catheter with the aforementioned beneficial features in accordance with presently preferred exemplary embodiments of the invention will be described below in detail with reference to FIGS. 1–11. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

FIG. 1 illustrates a multi-lumen multi-parameter catheter 10 for monitoring various heart functions in accordance with the present invention. The catheter comprises a flexible catheter tube 12 extruded from a biocompatible plastic material such as polyvinylchloride or polyethylene.

As shown in FIGS. 2A and 2B catheter 10 can be formed with a plurality of lumens. These lumen constructions can be accomplished by extrusion, molding or casting by conventional plastic processing operations or by other methods of catheter construction known to those skilled in the art. The catheter of the first preferred embodiment of FIG. 2A is a six lumen catheter which includes distal lumen 14, balloon inflation lumen 16, thermistor wire lumen 18, heater wire lumen 20, injectate lumen 22 and fiber optic lumen 24. As will be explained below, heater lumen 20 is also utilized to house a thermistor wherein a cross-over method is used to bring thermistor wires from lumen 18 over to lumen 20.

FIG. 2B illustrates a second preferred embodiment of the present invention wherein a novel seven lumen configuration is utilized permitting the catheter to include a large venous infusion port lumen 126. The catheter lumen configuration and relative sizes which are shown in FIG. 2B are provided in order to obtain maximum use of the cross-sectional area to permit the various diagnostic and/or therapeutic procedures for which the catheter is utilized. The elliptically shaped fiber optic lumen 124 is preferably oriented as shown in FIG. 2B with a major axis oriented to intersect the center of the catheter tube 12.

For example, distal lumen 114 is sized to permit either drug infusion, pressure monitoring, blood withdrawal, or guidewire passage during the catheterization procedure. Inflation lumen 116 is sized to permit balloon inflation. Heater wire lumen 120 is formed large enough to house the heater wires. Thermistor wire lumen 118 which houses thermistor leads is formed next to a larger lumen, for example, heater wire lumen 120, so that the larger thermistor bead can be housed in a larger lumen at the distal end of catheter 10 through a cross-over technique, which will be discussed below. Injectate lumen 122 is large to permit the fast injection of the liquid medium utilized to obtain cardiac output values through the bolus thermodilution technique.

Additionally, in the preferred embodiment of FIG. 2B, infusion lumen 126 is large enough to provide the necessary flow rates to permit fast infusion of drugs and other fluids. In an alternate embodiment, this lumen can house pacing wires for pacing the heart. In the preferred embodiment shown in FIG. 2B, fiber optic lumen 124 is elliptically shaped and located at the core of the catheter, but off center.

In a preferred embodiment, the foci of the ellipse is as close as possible to the center of the longitudinal axis of catheter tube 12. This lumen shape and position provides optimal cross-sectional area to accommodate the other lumens. Specifically, as is evident from FIG. 2B, smaller thermistor wire lumen 118 and balloon inflation lumen 116 are positioned next to one another to optimize utilization of the cross-sectional area of catheter tube 12 in light of the larger sizing for the other lumens. Smaller lumens 116 and 118 are positioned in an area where fiber optic lumen 124 is closest to outer wall 28 whereas the other larger lumens are located in an area where fiber optic lumen 124 is further from outer wall 28.

Furthermore, the lumen configuration of FIG. 2B enhances the catheter's mechanical resistance or integrity. This is accomplished by the formation, shaping, sizing and positioning of the catheter lumens between webs 30 which are formed and positioned such that forces imparted to the catheter by a catheter introducer are minimized, reducing the likelihood that the lumens or tube 12 will collapse inwardly. For example, crushing forces are transmitted by webs 30 to optical fiber lumen 124, which does not carry fluid but houses the optical fibers, and are distributed so as to cancel each other out.

Returning to FIG. 1, the distal end of catheter 12 includes a balloon 32 at the distal tip for flotation of catheter through the right atrium and right ventricle into the pulmonary artery. Balloon 32 is inflated through inflation lumen 16 or 116 by a coupling to an inflation means (not shown) via inflation connector 33 in accordance with principles and techniques well known to those skilled in the art.

At the proximal end of catheter 10 between catheter tube 12 and the various connectors is catheter manifold or backform 34 which couples catheter extension tubes 36, 38, 40, 42, 44, 46 and 48 to lumens 116, 114, 122, 124, 126, 118 and 120, respectively. Each of these extension tubes is elongated and flexible and has an axial passage therethrough. A preferred embodiment of a catheter backform and associated backform insert are disclosed in U.S. Pat. No. 4,670,009, to Bullock, which is incorporated by reference as if fully set forth herein.

Attached to the proximal end of extension tube 42 is optical connector 50 which provides optical interfacing between the optical fibers which fill optical fiber lumen 24 or 124 and an oximeter monitor (not shown). A plan view of optical connector 50 is illustrated in FIG. 3. Connector 50 typically has wall means which define an enclosure to house fiber optic means 52 and 54, such as optical fibers, to interface the fiber optic means 52 and 54 with an optics module (not shown) to an oximeter (not shown) in ways that are known to those skilled in the art. A preferred embodiment of optical connector 50 is disclosed in U.S. Pat. No. 4,647,149, to McCartney et al., which is incorporated by reference as if fully set forth herein. The fiber optic means 52 and 54 extend through fiber lumen 24 or 124 to transmit and receive optical signals to and from blood for the purposes of measuring oxygen saturation in ways that are known to those skilled in the art.

Figure 4:
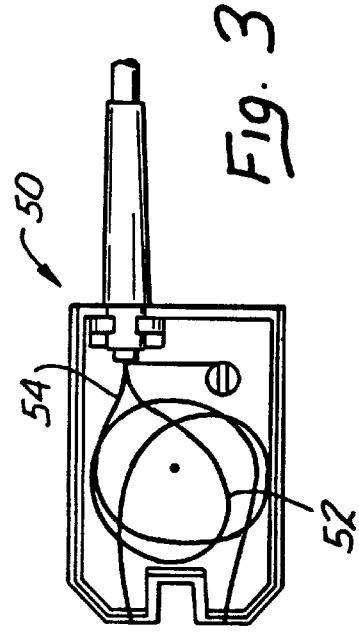
FIG. 4 illustrates a side elevational, partially sectioned view of the thermistor connector for use with the catheter of FIG. 1.

Attached to the proximal end of extension tube 46 is thermistor connector 56. FIG. 4 illustrates thermistor connector 56 in a plan, partial section. Thermistor wire leads 58 and 60 converge at thermistor wire 61 and extend through thermistor wire lumen 18 or 118 to thermistor bead 62, shown in FIG. 5. Thermistor connector 56 interfaces with a monitor to transmit the temperature measurements from thermistor bead 62 in ways well known to those skilled in the art. Thermistor bead 62 resides in a lumen near the distal tip of the catheter for taking temperature measurements for both bolus cardiac output and continuous cardiac output measurements. In a preferred embodiment, thermistor bead 62 resides in a lumen that is larger than thermistor wire lumen 18 or 118 and a cross-over technique is utilized to connect the thermistor leads 58 and 60 to thermistor bead 62.

The thermistor wire cross-over feature mentioned above is shown in FIG. 6, which shows thermistor wire 61 extending through thermistor wire lumen 18 and passing through cross-over port 63 into adjacent lumen 20 where it is attached to thermistor bead 62, which is not shown in FIG. 6. Thermistor bead 62 is thereby exposed to the flowing blood through thermistor port 64. An example of this cross-over technique is disclosed in U.S. Pat. No. 4,329,993, to Lieber et al.

Figure 6:
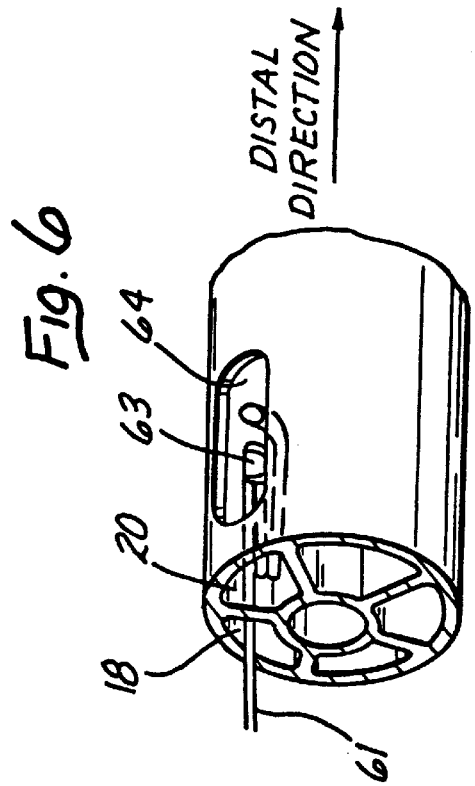
FIG. 6 illustrates a perspective view of the catheter portion shown in FIG. 5 which has been sliced to show the cross-over of the thermistor wires.

The cross-over feature of FIG. 6 is shown with the six lumen cross-section configuration of FIG. 2A. However, the cross-over feature can also be used with the seven lumen embodiment of FIG. 2B by bringing thermistor wire 61, which extends through lumen 118 into adjacent lumen 120 through an analogous cross-over port. Thermistor bead 62 resides in lumen 20 or 120 which is sufficiently large to house it and in a position distal to the heater so that the heater wires no longer occupy the lumen.

In yet another preferred embodiment of the present invention, thermistor bead 62 is small enough that it can be placed in a smaller lumen. For example, thermistor bead 62 could be housed in lumen 118 so that thermistor wire 61 will extend all the way through lumen 118 until it directly couples with thermistor bead 62 without using a cross-over technique. Alternatively, thermistor wire 61 could be placed with the optical fibers 52 and 54 in a lumen that is adjacent wall 28 so as to couple with thermistor bead 62 at the outer periphery of catheter tube 12. This would provide more cross-sectional area for other lumen configurations.

Attached to the proximal end of extension tube 48 is heater connector 65 which is further illustrated in FIG. 7. Heater wires 66 fun from heater connector 65 through heater wire lumen 20 or 120 to heater 68, which in a preferred embodiment is a flat heater ribbon heating filament wound around the outside of catheter tube 12 as shown in FIG. 8. However, other heating elements known in the art may also be used such as a heater wire wound around the catheter tubing. Heater 68 is used to transmit a heat signal into blood for the purpose of measuring cardiac output continuously. A preferred method of calculating cardiac output in this fashion is disclosed in U.S. Pat. No. 5,146,414 to McKown et al.

In a preferred embodiment, radiopaque markers are placed distal and proximal to heater 68 to provide for x-ray locationing to assist with catheter positioning for purposes of both safety and efficacy. Furthermore, as discussed above with respect to the thermistor wire cross-over feature, heater wires 66 terminate at heater element 68 and do not proceed through lumen 20 or 120 which is now free to house thermistor bead 62.

Heater connector 65 also includes a memory component 70, such as a ROM (Read Only Memory) or EPROM, RAM (Random Access Memory), nonvolatile memory devices or other types of memory or digital devices containing calibration information. This information could be catheter and/or patient calibration information. In a preferred embodiment, heater 68 is a self-monitoring device comprising a resistive heater having a thermal coefficient of resistance that permits the temperature of the heater to be known and controlled by monitoring the resistance value. Such a heater is disclosed in U.S. patent application Ser. No. 08/049,231, to Quinn et al. In this instance, memory component 70 includes calibration information that relates to filament resistance, filament efficiency, and other parameters.

In a preferred embodiment, heater 68 is affixed to a stepped-down region 72 of catheter tube 12 wherein the diameter of catheter tube 12 is reduced to accommodate heater 68. Stepped-down region 72 is shown without heater 68 in FIG. 9. When heater 68 is affixed to stepped-down region 72 the resultant outer diameter of catheter tube 12 is fairly consistent throughout the distal tubing length as seen in FIG. 8. This permits catheter 10 to be inserted into a patient without creating trauma that could result if heater 68 created a thickened region.

Figure 10:
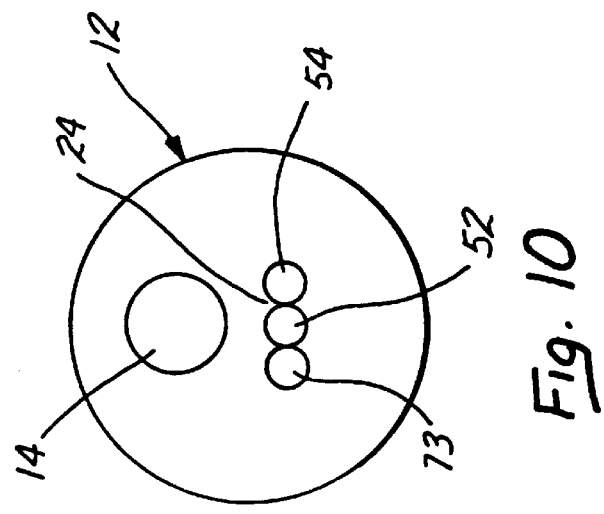
FIG. 10 illustrates a cross-sectional view of the catheter taken along the lines 10—10 of FIG. 1, showing the lumen configuration at the tip of the catheter of the present invention.

FIG. 10 illustrates a cross-sectional view of the tip of the catheter of the present invention showing distal lumen 14 and optical fiber lumen 24 with optical fibers 52 and 54 and a spacer fiber 73. Distal lumen 14 is a through lumen which can be used to infuse fluids or medication, monitor pressure, withdraw blood or house a guidewire for catheter placement. As discussed above, lumen 24 houses optical fibers 52 and 54 which transmit and receive light signals at the distal tip of catheter 10 for oxygen saturation measurements in accordance with principles known to those skilled in the art.

Returning to FIG. 1, attached to the proximal ends of extension tubes 38, 40 and 44 are lumen hubs 74, 76, and 78, respectively. These lumen hubs are preferable luer locks for connecting these extension tubes to fluid sources, pressure monitoring devices, pacing devices or other therapeutic or diagnostic devices which could utilize the lumens disclosed herein in the ways discussed above and in ways known to those skilled in the art.

Figure 5:
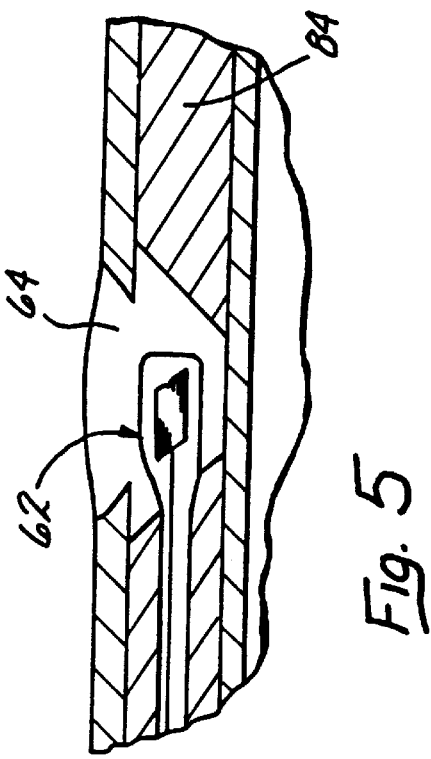
FIG. 5 illustrates a side elevational view, in cross-section of the distal end of the catheter of FIG. 1 showing the thermistor bead.
Figure 11B:
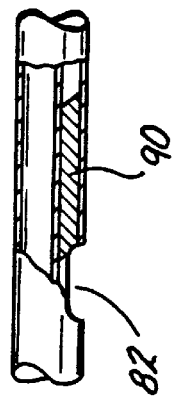
FIG. 11B illustrates an enlarged side elevational view, partially cut away, of a portion of the catheter of FIG. 11 proximate an infusion port.
Figure 11A:
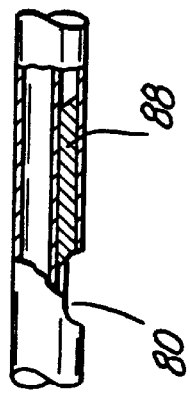
FIG. 11A illustrates an enlarged side elevational view, partially cut away, of a portion of the catheter of FIG. 11 proximate an injectate port.
Figure 11:
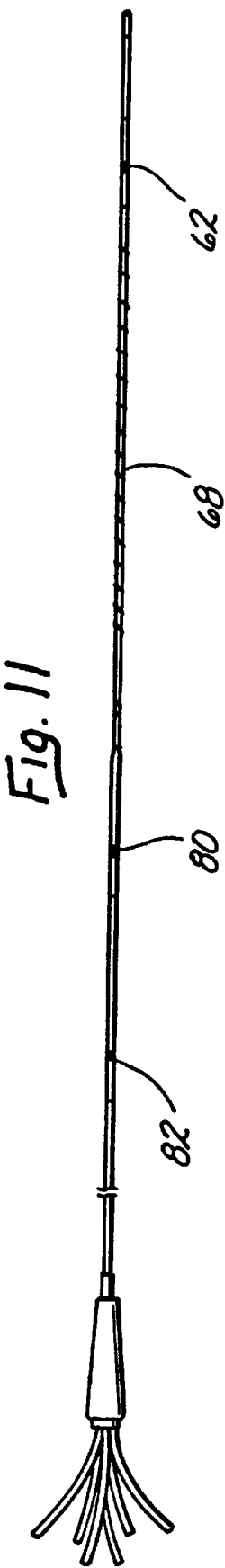
FIG. 11 illustrates a side elevational view of a preferred embodiment of the catheter of the present invention showing the relative positions of the heater element, infusion port and injectate port.

Turning to FIG. 11, we see the relative location of heater 68, thermistor 62, injectate port 80 and infusion port 82. Thermistor 62 is located between 3.5 and 4.5 centimeters from the distal tip of catheter 10. As discussed above, thermistor bead 62 resides in lumen 18 or 118 and is exposed to the flowing blood through thermistor port 64. Placement and potting of thermistor bead 62 in lumen 18 is accomplished through techniques which are well known to those skilled in the art. Lumen 18 typically contains plug 84 on the distal side of thermistor bead 62 as shown in FIG. 5.

In a preferred embodiment heater 68 comprises a flat ribbon heating filament which is wound around the outside of catheter tube 12 and extends 10–15 cm along the catheter length, beginning between 10–15 cm from the distal tip of catheter 10. In a preferred embodiment, heater 68 begins 14 cm from the distal tip of catheter 10, at a point 10 cm proximal to thermistor 62, and extends 10 cm to a point 24 cm from the distal tip.

In a preferred embodiment, the ribbons of heater 68 are wound around catheter tube 12 so that the centers of individual ribbons 86 are evenly spaced apart as shown in FIG. 8. In a preferred embodiment, ribbons 86 are spaced apart a minimum of 0.02 cm. Heater ribbons 86 are typically spaced apart between 0.02 and 0.50 cm.

At about 26 cm from the distal tip of catheter 10, upstream from thermistor 62, is an injectate port 80 which communicates with injectate lumen 22 or 122. In a preferred embodiment injectate port 80 is located 2 cm proximal to heater 68. As discussed above, injectate port 80 is utilized for injection of a liquid medium to obtain cardiac output values through the bolus thermodilution technique. As shown in FIG. 11A, injectate lumen 22 includes a plug 88, preferably of PVC, distal to port 80 to direct injectate flow from lumen 22 and out through injectate port 80. In an alternate preferred embodiment, due to the size of injectate lumen 22 or 122, injectate port 80 could be utilized to infuse medication, withdraw blood or even to monitor pressure at that position.

In a preferred embodiment, catheter 10 includes an infusion port 82 which communicates with infusion lumen 126. Port 82 is preferably located proximal to heater 68 and in a preferred embodiment is located 30 cm from the distal tip of catheter 10. As discussed above and as shown in FIG. 2B, infusion lumen 126 is sufficiently large enough to permit fast infusion of solutions into the bloodstream. As shown in FIG. 11B, infusion lumen 126 includes a plug 90, preferably of PVC, distal to port 80 to direct infusion flow from lumen 126 and out through infusion port 80.

Thus, what is provided by the present invention is a multi-lumen, multi-parameter catheter which is capable of combining numerous diagnostic and therapeutic features. A unique lumen configuration provides a catheter which can accommodate numerous features without sacrificing durability or exceeding clinically acceptable size constraints. Those skilled in that art will recognize that the lumen cross-sections disclosed herein could be utilized in alternate ways. For example, the functions of heater wire lumen 120 and distal lumen 114 could be exchanged which could result in an exchange of function between inflation lumen 116 and thermistor wire lumen 118, if a cross-over of thermistor wire is desired. Other such exchanges of lumen functions are possible and would be evident to one skilled in the art.

In closing it is to be understood that the embodiments of the invention disclosed herein are illustrative of the principles of the invention and that other modifications may be employed which are within the scope thereof. Accordingly, the present invention is not limited to that precisely as shown and described in the specification, and any modifications, variations or equivalent arrangements within the scope of the attached claims should be considered to be within the scope of the invention.

We claim:

1. A multi-lumen catheter system configured to accommodate various diagnostic and therapeutic procedures, comprising:
    a flexible elongated tubing portion having a longitudinal axis, an exterior wall and defining multiple lumens therein, including:
        an interior lumen positioned off-center with respect to the longitudinal axis to be closer to a first side of the exterior wall, and farther from a second side of the exterior wall opposite the first side, wherein the interior lumen is elliptically shaped in cross-section;
        a plurality of outer lumens defined within the tubing portion surrounding the interior lumen and generally between the interior lumen and the exterior wall, a pair of the outer lumens being positioned between the interior lumen and the first side and having smaller cross-sectional areas than the other outer lumens for an efficient lumen space utilization, and at least one outer lumen being larger than the interior lumen and being positioned generally between the interior lumen and the second side, wherein the offset interior lumen accommodates the differing sized outer lumens to optimize their relative sizes and positions.

2. The multi-lumen catheter system of claim 1, wherein the number of outer lumens equals at least six.

3. The multi-lumen catheter system of claim 1, wherein one of the pair of outer lumens comprises an inflation lumen sized to permit passage of an inflation fluid, the catheter further including a balloon affixed to the distal tip of the tubing portion wherein the inflation lumen is in fluid communication with the interior of the balloon.

4. The multi-lumen catheter system of claim 1, wherein one of the pair of outer lumens is sized to permit passage of a temperature measuring wire, the catheter further including a temperature measuring sensor positioned proximate the distal end of the tubing portion and in communication with a monitor via the temperature measuring wire.

5. The multi-lumen catheter system of claim 4, further including a cross-over port formed between the one of the pair of outer lumens and an adjacent outer lumen, the cross-over port allowing passage of the temperature measuring wire, the temperature measuring sensor comprising a thermistor bead positioned in the adjacent outer lumen and in electrical communication with the temperature measuring wire.

6. The multi-lumen catheter system of claim 1, wherein the interior lumen has a first focus proximate to the longitudinal axis of the tubing portion.

7. The multi-lumen catheter system of claim 1, wherein the interior lumen is a fiber optic lumen.

8. The multi-lumen catheter system of claim 7, wherein the pair of outer lumens define:
    an inflation lumen having a smaller cross-sectional area than the fiber optic lumen, and catheter includes a balloon affixed to the distal tip of the tubing portion wherein the inflation lumen is in fluid communication with the interior of the balloon; and
    a wire-conduit lumen having a smaller cross-sectional area than the fiber optic lumen.

9. The multi-lumen catheter system of claim 8, wherein the catheter includes a temperature measuring sensor positioned proximate the distal end of the tubing portion and in communication with a monitor via a temperature measuring wire positioned in the wire-conduit lumen.

10. The multi-lumen catheter system of claim 9, wherein the outer lumens other than the pair define:
    a heater wire lumen having a cross-sectional area larger than the fiber optic lumen, and the catheter system includes a heater connected via wires extending through the heater wire lumen to a heating filament wound around the exterior wall;
    a distal lumen having a cross-sectional area larger than the heater wire lumen and extending to the distal end of the tubing portion to permit passage of a guidewire;
    an injectate lumen having a cross-sectional area larger than the heater wire lumen and terminating in an injectate port through the exterior wall and located proximally from the temperature measuring sensor; and
    an infusion lumen having a cross-sectional area larger than all of the other lumens and terminating in an infusion port through the exterior wall and located proximally from the injectate port.

11. The multi-lumen catheter system of claim 8, wherein the catheter system includes a heater connected via wires extending through the wire-conduit lumen to a heating filament wound around the exterior wall.

12. A multi-lumen catheter system configured to accommodate various diagnostic and therapeutic procedures, comprising:
    a flexible elongated tubing portion having an exterior wall and a plurality of webs defining multiple lumens within the catheter, including:
        an interior, fiber optic lumen elliptically shaped in cross-section and positioned off-center to be closer to a first side of the exterior wall, and farther from a second side of the exterior wall opposite the first side; and a plurality of outer lumens surrounding the fiber optic lumen and generally between the fiber optic lumen and the exterior wall, a pair of the outer lumens being positioned generally between the fiber optic lumen and the first side of the exterior wall and sized smaller in cross-sectional area than the other outer lumens for an efficient lumen space utilization, and at least one outer lumen being larger than the fiber optic lumen and being positioned generally between the fiber optic lumen and the second side of the exterior wall opposite the first side, wherein the relative sizes and positions of the lumens between the webs enhances use of the cross-sectional area and kink-resistance of the catheter.

13. The multi-lumen catheter system of claim 12, wherein the fiber optic lumen has a first focus proximate to the longitudinal axis of the tubing portion.

14. The multi-lumen catheter system of claim 12, further including a plurality of optical fibers substantially filling the fiber optic lumen so that when forces are imparted to the exterior wall they are transmitted through the webs on one side of the fiber optic lumen and across the fiber optic lumen to the webs on the opposite side of the fiber optic lumen and to the exterior wall by virtue of the solid optical fibers within the fiber optic lumen.

15. The multi-lumen catheter system of claim 12, wherein the outer lumens other than the pair define:

a heater wire lumen having a cross-sectional area larger than the fiber optic lumen, and the catheter system includes a heater connected via wires extending through the heater wire lumen to a heating filament wound around the exterior wall;

a distal lumen having a cross-sectional area larger than the heater wire lumen and extending to the distal end of the tubing portion to permit passage of a guidewire;

an injectate lumen having a cross-sectional area larger than the heater wire lumen and terminating in an injectate port through the exterior wall and located proximally from the heating filament; and an infusion lumen having a cross-sectional area larger than all of the other lumens and terminating in an infusion port through the exterior wall and located proximally from the injectate port.

* * * * *